United States Patent [19]

Gross et al.

[11] Patent Number: 5,079,354
[45] Date of Patent: Jan. 7, 1992

[54] METHOD FOR MAKING ABSORBENT STARCH

[75] Inventors: James R. Gross, Appleton, Wis.; Michael P. Greuel, Akron, Ohio

[73] Assignee: Kimberly-Clark Corporation, Neenah, Wis.

[21] Appl. No.: 428,133

[22] Filed: Oct. 27, 1989

[51] Int. Cl.$^5$ .................. C08B 31/08; C08B 33/04; C08B 35/04
[52] U.S. Cl. ..................... 536/111; 536/124
[58] Field of Search .................. 536/111, 124

[56] References Cited

U.S. PATENT DOCUMENTS

| | | | |
|---|---|---|---|
| Re. 31,323 | 7/1983 | Marder et al. | 536/87 |
| 2,639,239 | 5/1953 | Elliott | 106/197 |
| 2,772,999 | 12/1956 | Masci et al. | 167/84 |
| 3,345,358 | 10/1967 | Inkaar | 536/106 |
| 3,347,236 | 10/1967 | Torr | 128/284 |
| 3,379,720 | 4/1968 | Reid | 536/87 |
| 3,678,031 | 7/1972 | Schoggen | 536/98 |
| 3,723,413 | 3/1973 | Chatterjee et al. | 536/87 |
| 3,935,099 | 1/1976 | Weaver et al. | 210/43 |
| 3,981,100 | 9/1976 | Weaver et al. | 47/58 |
| 4,117,222 | 9/1978 | Holst et al. | 536/111 |
| 4,454,055 | 6/1984 | Richman et al. | 252/194 |
| 4,483,950 | 11/1984 | Fanta et al. | 524/48 |

FOREIGN PATENT DOCUMENTS 1550614  8/1979  United Kingdom .

Primary Examiner—Nathan M. Nutter
Attorney, Agent, or Firm—Thomas J. Mielke

[57] ABSTRACT

A method for producing a water-swellable, water-insoluble carboxyalkyl starch. The steps of the method involving forming an aqueous dispersion of starch; adding to said aqueous dispersion carboxyalkylating reactants under conditions sufficient to form a water-soluble carboxyalkyl starch having an average degree of substitution between about 0.25 and 1.5; and recovering the carboxyalkyl starch by evaporative drying at a temperature within the range of from about 50° C. to about 150° C.

24 Claims, No Drawings

METHOD FOR MAKING ABSORBENT STARCH

BACKGROUND OF THE INVENTION

1. Field of the Invention

The present invention relates to a process for forming a highly absorbent starch and the product formed by said process.

2. Description of the Related Art

Formation of carboxymethyl starch is known to those skilled in the art. As a general rule, carboxymethyl starch is suitably prepared by the reaction of starch with an alkali metal hydroxide such as sodium hydroxide whereby alkali starch is formed. The alkali starch is then reacted with a chloroalkanoic acid such as monochloroacetic acid to form the carboxymethyl starch. As normally produced, the carboxymethyl starch is water-soluble. Accordingly, the carboxymethyl starch is generally produced and recovered from a non-aqueous media such as an alcohol. The carboxymethyl starch so produced is known for use as a water-soluble thickening agent.

Unfortunately, the degree of thickening achievable through the use of the carboxymethyl starch described above is limited. For numerous applications it is desirable to employ a thickening agent with greater thickening powers than can be achieved with conventional carboxymethyl starch. Accordingly, U.S. Pat. No. 3,345,358 issued Oct. 3, 1967 to Inklaar describes a method of preparing a gel-forming derivative of polysaccharides such as carboxymethyl starch. The method involves acidifying finely divided carboxymethyl ethers of polysaccharides by treating them with acid in methanol or other water-miscible organic liquid medium. In this manner acid carboxymethyl groups are formed on the material. The material is held under acidified, non-hydrolyzing conditions to bring about the formation of ester bonds whereby constituent macro molecules of the material become crosslinked one to another. The material is then neutralized with an alkali. The derivatives so produced are described as being capable of forming a gel upon addition to water. The gels are described as having a smooth creamy or salve-like consistency and as being easily spreadable. The gels are useful as bodying, gelling, emulsifying, suspending or thickening agents for a wide variety of aqueous liquids.

Great Britain Patent No. 1 550 614 published Aug. 15, 1979 describes an absorbent material suitably formed from starch. Described is the crosslinking of starch with a chloroalkyl oxirane such as epichlorohydrin. The crosslinked starch is then treated with sodium hydroxide and monochloroacetic acid and slurried in hydrochloric acid to recover the starch-based absorbent.

Both of the above references described methods for producing crosslinked starch derivatives. Unfortunately, both of the references describe methods which are generally cumbersome in that they involve multiple steps. Specifically, the first reference involves a separate acidifying step with the second reference describing the use of a crosslinking agent to crosslink the starch prior to forming a starch derivative. It is desirable to provide a direct method for forming a crosslinked starch derivative which method is less cumbersome than the methods previously described.

U.S. Pat. No. 3,379,720 issued Apr. 23, 1968 to Reid is directed to water-soluble polymers and the process of preparing such polymers. Reid describes a process of preparing water-soluble polymers which can be rendered water-insoluble by curing. The method describes acidifying ethers and esters of polysaccharides which contain carboxylate groups, such as cellulose, starch and natural gums, until the ratio range of the free acid form to the salt form of its carboxyl groups is about 0.07 to 1-3 to 1, removing the excess acid and drying. The resultant modified polysaccharide is described as being water-soluble and capable of being insolublized by curing. Again, Reid describes a method involving a separate acidification step.

U.S. Pat. No. 4,483,950, issued Nov. 20, 1984, to Fanta et al., describes using highly modified, low molecular weight starches as extenders for starch-based superabsorbents. Dextrinized starches are described as synergistically interacting with the superabsorbents to permit dilution without a commensurate reduction in the water absorbency.

U.S. Pat. Nos. 3,981,100, issued Sept. 21, 1976 and 3,935,099, issued Jan. 27, 1976, to Weaver et al. describe absorbent starch-containing polymeric composition which are prepared by graft polymerizing acrylonitrile onto starch followed by saponification of the starch-poly(acrylonitrile) graft polymer. The sponified polymer may then be recovered by drying.

SUMMARY OF THE INVENTION

It is desirable to produce a water-swellable, water-insoluble derivative of carboxylalkyl starches through a method which is both simple and economical. Such water swellable, water-insoluble starch derivatives would be suitable for use in a variety of absorbent applications. Further, it is desirable that the method employed in making the described starch derivatives employ nonorganic solvents, thus rendering the process safer and more economic.

These and other related goals are achieved in a process of forming a water-swellable, water-insoluble carboxyalkyl starch derivative which process comprises the steps of:

(a) forming an aqueous dispersion of starch comprising from about 10 to about 40 weight percent starch based on total weight of the aqueous dispersion;

(b) adding to said aqueous dispersion carboxyalkylating reactants under conditions sufficient to form a water-soluble carboxyalkyl starch having an average degree of substitution between about 0.25 and about 1.5; and (c) recovering the carboxyalkyl starch by evaporative drying at a temperature within the range of from about 50° to about 150° C. whereby a water-swellable, water-insoluble cross-linked starch derivative is formed.

DETAILED DESCRIPTION OF THE PREFERRED EMBODIMENT

The present invention relates to a method of producing water-swellable water-insoluble carboxyalkyl starch derivatives.

As used herein, the term "starch" refers to a carbohydrate polymer having repeating anhydroglucose units and is intended to encompass amylose or amylopectin alone or any combination of amylose and amylopectin, as well as starch in a more common sense derived from any source (e.g. starch derived from corn, potatoes, tapioca, rice, wheat, sorghum, and the like). Starch is generally water soluble in hot water.

According to the method of the present invention, 10 to 40 weight percent, preferably about 15 to about 30 weight percent of starch is dispersed in water to form an aqueous dispersion. To the starch-containing aqueous dispersion is then added carboxyalkylating reactants. As used herein, reference to the term "carboxyalkylating reactants" is intended to refer to a combination of one or more reactants which are capable of converting starch into carboxyalkyl starch.

By way of example, the term "carboxyalkylating reactants" is intended to encompass the combination of ammonium hydroxide or an alkali metal hydroxide (such as sodium hydroxide) and a haloalkanoic acid such as monochloroacetic acid. In practice, the ammonium hydroxide or alkali metal hydroxide is added to the starch containing aqueous dispersion to form an ammonium or alkali starch (in solution). The alkali starch is then treated with the haloalkanoic acid to form a carboxyalkyl starch.

Exemplary of the alkali metal hydroxides suitable for use in the present invention are sodium hydroxide, potassium hydroxide, and lithium hydroxide. Due to considerations of safety and cost, the alkali metal hydroxide preferred for use in the present invention is sodium hydroxide.

As a general rule, the ammonium or alkali metal hydroxide is added to the starch containing aqueous dispersion in an amount of from about 25 to about 300 mole percent based on the total amount of starch present in said starch containing aqueous dispersion. Preferably, the ammonium or alkali metal hydroxide is present in an amount such that there is a slightly more than two equivalents of ammonium or alkali metal hydroxide present per mole of haloalkanoic acid used. The ammonium or alkali metal hydroxide is generally mixed in the starch containing aqueous dispersion while the dispersion is maintained at ambient temperature (generally within the range of from about 15° to about 30° C.).

An amount of a haloalkanoic acid is then added to the aqueous dispersion. Haloalkanoic acids suitable for use in the present invention include monohaloacetic acid such as monochloroacetic acid, and monobromoacetic acid; monohalomaleic acid such as monochloromaleic acid, and monobromomaleic acid; monohalomalonic acid such as monochloromalonic acid and monobromomalonic acid; monohalosuccinic acid such as monochlorosuccinic acid and monobromosuccinic acid; and the like. For reasons such as cost and safety, the preferred haloalkanoic acid for use in the present invention is monochloroacetic acid.

The haloalkanoic acid is suitably added to the aqueous dispersion in an amount sufficient to form a carboxyalkyl starch having a degree of substitution of from about 0.25 to about 1.5, preferably from about 0.5 to about 1.25. As used herein, reference to the degree of substitution refers to the average number of carboxyalkyl groups present on each repeating anhydroglucose unit. Those skilled in the art will recognize that the repeating anhydroglucose units of starch each possess three hydroxyl groups. Accordingly, the maximum degree of substitution is three. In such a case, each repeating anhydroglucose unit of the starch is converted to possess three carboxyalkyl groups. Clearly, when the degree of substitution is less than one, not every repeating anhydroglucose unit of the starch molecule has a carboxyalkyl group.

As a general rule, the haloalkanoic acid will be added to the aqueous dispersion in an amount of from about 25 to about 150 mole percent based on total moles of anhydroglucose repeating units present in the aqueous dispersion. After addition of the haloalkanoic acid the aqueous dispersion is suitably maintained at a temperature within the range of from about 25° to about 100° C. for a period of from about 2 to about 24 hours.

The above described process results in the conversion of a substantial portion of the starch present in the aqueous dispersion into a carboxyalkyl starch. Specifically, when sodium hydroxide is employed as the alkali metal hydroxide and monochloroacetic acid is employed as the chloroalkanoic acid, the carboxylalkyl starch produced is carboxymethyl starch.

As a general rule, prior methods of producing carboxymethyl starch have employed an organic solvent such as an alcohol in which to perform the carboxyalkylation process. Alcohols have been employed as the solvent because the carboxylalkyl starch so produced is water soluble. Since carboxyalkyl starches are generally not soluble in organic solvents the use of an organic solvent allowed for easier recovery of the carboxyalkyl starch. The present invention employs water as the solvent.

The aqueous solution containing the carboxyalkyl starch formed as described above is suitably, optionally, adjusted to a pH within the range of from about 5 to about 13.5. It is understood that careful selection of the carboxyalkylating reactants may produce a carboxyalkyl starch-containing solution having a pH within the described ranges thus rendering a specific adjustment step unnecessary. However, if the pH is outside the preferred range, the pH may be adjusted by adding appropriate quantities of bases such as sodium hydroxide, ammonium hydroxide, potassium hydroxide, and the like or acids such as hydrochloric, nitric, sulfuric, and the like. The described range is preferred because it has been found to produce the best balance between the degree of crosslinking (and consequently, absorptive capacity) and structural integrity (gel stiffness). As a general rule, at pH's below about 5 the modified starch undergoes too high a degree of crosslinking upon drying to possess a desireable absorptive capacity. At pH's above about 13.5, the modified starch does not undergo sufficient crosslinking to provide it with a desireable degree of structural integrity.

The carboxyalkyl starch is then recovered from the aqueous reaction medium by evaporative drying at a temperature within the range of from about 50° to about 150° C. preferably, within the range of from about 80° to about 125° C.

The inventors have discovered that the evaporative drying of the carboxyalkyl starch at the elevated temperatures described herein leads to self crosslinking between the carboxyalkyl starch molecules. It is believed that the mechanism of the self crosslinking is a result of the direct esterification between a hydroxyl group of one starch molecule and the carboxyalkyl ether group on a second starch molecule. This is evidenced by the fact that carboxyalkyl starch prepared in accordance with the above described method demonstrates a second carbonyl band at about 1740 cm$^{-1}$ under infrared analysis. The second carbonyl band could be attributed to the ester formation. When the carboxyalkyl starch is formed as described above but is recovered from the aqueous solution by drying at room temperature, the second carbonyl band is not demonstrated during infrared analysis.

Any means of accomplishing the drying should be operable as long as the drying time and drying temperature are selected so that the desired degree of crosslinking occurs. Exemplary of suitable means of performing the evaporative drying are, convection ovens, vacuum ovens, drum dryers, devolatilizing extruders or other continuous processes involving microwave heat, infrared heat, or the like.

Prior art methods of forming crosslinked carboxyalkyl starches have employed crosslinking agents. The use of crosslinking agents can be avoided through the evaporative drying at elevated temperatures as described above.

The crosslinked carboxyalkyl starches produced by the method of the present invention are suitable for use in absorbent products such as diapers, adult incontinent garments, sanitary napkins, bandages, and the like. When the modified starches of the present invention are, for example, to be incorporated into a diaper the polymeric material will generally be in particulate form, such as flakes, spheres, irregularly shaped particles and the like. The modified starch particles will generally be located within and carried by a fibrous web. The fibrous web can, for example, be made from cellulosic fibers such as wood pulp fluff or may be formed from synthetic fibers such as polyolefin fibers or mixtures of polyolefin fibers and wood pulp fluff. As a general rule, the diaper will comprise an outer water-impervious liner, an absorbent core comprising a fibrous web containing the modified starch material of the present invention, and a water-pervious bodyside liner adapted to contact the skin of the wearer. The fibrous web is sandwiched between the outer liner and the bodyside lines. Such products are generally described in U.S. Pat. Nos. 4,710,187, issued Dec. 1, 1987 to Boland et al.; 4,762,521 issued Aug. 9, 1988 to Roessler et al.; 4,770,656 issued Sept. 13, 1988, to Proxmire et al.; and 4,798,603 issued Jan. 17, 1989 to Meyer et al.; which references are hereby incorporated by reference.

Additionally, applicants have discovered that the modified starches of the present invention may be extended with unmodified starch thus significantly reducing the raw material costs of the absorbent material prepared by the process of the present invention. Specifically, when solutions of starch derivatives prepared according to the process of the present invention are mixed with gelatinized starch and then subjected to evaporative drying as described above, the starch is believed to function as an interactive filler which reacts with the carboxyalkyl groups to form a starch grafted carboxyalkyl starch derivative. The gelatinized starch may be added to the solutions of starch derivatives as gelatinized starch or may be added to the solutions of starch derivatives as unmodified starch with the solutions then being heated to about 70°-100° C. to gelatinize the starch prior to evaporative drying.

For example, prior to drying, the gelatinized starch (or unmodified starch which is gelatinized prior to evaporative drying) can be mixed with the water-soluble carboxyalkyl starch prepared as described above in an amount of from about 1 to about 50 weight percent preferably, in an amount of from about 20 to about 40 weight percent based on the total amount of water-soluble carboxyalkyl starch present in the aqueous solution. The carboxyalkly starch is then recovered from the aqueous dispersion through evaporative drying at the elevated temperatures described above. The gelatinized starch must be added to the carboxyalkyl starch before it is subjected to the evaporative drying at an elevated temperature according to the process of the present invention. Once the carboxyalkyl starch is subjected to the evaporative drying the crosslinked starch so produced forms a gel upon mixing with water thus precluding formation of the grafted carboxyalkyl starch.

The present invention can best be understood with reference to the following examples which examples are not intended to limit, in any way, the scope of the invention as set forth in the claims.

EXAMPLE 1

Twenty-five (25) grams of amylose corn starch commercially available from National Starch under the tradename Hylon VII is slurried into 50 grams of distilled water. To the mixture of cornstarch and water is added 8.5 grams of sodium hydroxide which has been dissolved in 50 grams of distilled water. The resulting solution is allowed to stand at room temperature for 60 minutes. To this solution is then added 9.75 grams of monochloroacetic acid which has been dissolved in 10 grams of distilled water. The resultant solution is covered and allowed to stand overnight without heating or stirring. After standing, the solution is found to have a viscosity of 1,640 centipoise at 25° C. (Brookfield RVT, #5 spindle, 50 revolutions per minute). A 30 mil coating of the solution on glass is placed in a 90° C. vacuum oven (15 inches of mercury, air bleed) overnight. Evaporative drying is found to produce large flakes of crosslinked carboxymethyl starch. The carboxymethyl starch has a calculated degree of substitution of 0.67.

The absorbent capacity of the resultant cross-linked carboxymethyl starch is determined by soaking, with occasional stirring, for thirty minutes, a portion of the recovered crosslinked carboxymethyl starch in one hundred parts of water or saline solution (aqueous solution containing 1 weight percent sodium chloride) per part of carboxymethyl starch. The starch is found to have an absorbent capacity of 22 grams of liquid per gram of starch in an aqueous solution containing 1 weight percent sodium chloride and an absorbent capacity of 41 grams of liquid per gram of starch in distilled water.

EXAMPLE 2

The procedure of Example 1 is repeated using ordinary corn starch (combination of amylose and amylopectin) instead of amylose corn starch. The ordinary corn starch is commercially available under the trade designation Argo ™. The alkaline starch solution is held 30 minutes before blending with the chloroacetic acid instead of 60 minutes as set forth in Example 1. The final solution, after standing overnight, is found to have a viscosity of 30,000 centipoise as determined according to the procedure set forth in Example 1. After drying for 4 hours in a vacuum oven (80° C., 15 inches of mercury), the carboxymethyl starch is found to have an absorbent capacity of 40 grams of liquid per gram of starch in an aqueous solution containing 1 weight percent sodium chloride. When a 30 mil coating of the solution is dried for 30 minutes in a 90° convection oven the resultant carboxymethyl cellulose is found to have an absorbency of 25 grams of liquid per gram of polymer in an aqueous solution containing 1 weight percent sodium chloride.

EXAMPLE 3

In order to determine the effect of the pH of the solution the following experiment is conducted. Twenty-five grams of ordinary cornstarch (amylose and amylopectin) is slurried in 100 milliliters of distilled water to form a starch slurry. To this starch slurry is added 8.5 grams of sodium hydroxide which has been dissolved in 50 milliliters of distilled water, to form an alkaline starch solution. The alkaline starch solution is stirred for 30 minutes, while being maintained at room temperature. To the alkaline starch solution is then added 9.75 grams of monochloroacetic acid which has been dissolved in 10 milliliters of water, to form a final solution. The final solution is stirred for six hours and is maintained at 50° C. It is noted that the pH of the solution during the six hour period of stirring gradually drops, leveling off at approximately 12.25. After six hours of stirring the final solution is calculated to be 15% sodium carboxymethyl starch by weight. After cooling to room temperature, the final solution is found to have a pH of 13.1.

Four individual samples of the resultant solution are then dried in a vacuum oven for 30 minutes at 100° C. The vacuum oven is maintained at 15 inches of mercury with an air bleed. In order to determine the effect of pH on the sodium carboxymethyl starch, the four samples of the final solution are adjusted to various pH's with hydrochloric acid prior to drying. The pH of the various samples is set forth in Table 1. After drying, the absorbency of the four samples of sodium carboxymethyl starch is determined according to the process set forth in connection with Example 1. The absorbency is determined in an aqueous solution containing 1 weight percent sodium chloride. The absorbency data for the samples is similarly set forth in Table 1.

TABLE 1

| SAMPLE | pH | ABSORBENCY (g/g) |
|---|---|---|
| 1 | 13.1 | 29.2 |
| 2 | 12.1 | 17.4 |
| 3 | 11.1 | 15.5 |
| 4 | 3.5 | 11.8 |

As can be seen from reference to Table 1, as a general rule, the lower the pH the more crosslinked is the sodium carboxymethyl starch and the lower the absorbency on a gram per gram basis.

EXAMPLE 4

The procedure of Example 3 is repeated except that after addition of the monochloroacetic acid the final solution is stirred for five hours and 20 minutes. The final solution is then allowed to cool to room temperature and is aged either for a period of 4.0–4.5 hours or for a period of 24 hours. Prior to drying, the solution is adjusted to a pH of 4.3 by the addition of hydrochloric acid. Four samples of the solution are then dried in a vacuum oven (15 inches of mercury, air bleed) for one hour or in a 125° C. convection oven for 15 minutes. The exact drying conditions are set forth in Table 2. The absorbency of the resultant sodium carboxymethyl cellulose in an aqueous solution containing 1 weight percent sodium chloride is then determined according to the process set forth in Example 1. The absorbency is set forth in Table 2.

TABLE 2

| SAMPLE | pH | AGING PERIOD | DRYING TIME | DRYING TEMPERATURE | ABSORBENCY (g/g) |
|---|---|---|---|---|---|
| 1 | 4.3 | 4.5 hrs. | 60 min. | 90° C. | 13.3 |
| 2 | 4.3 | 4.0 hrs. | 15 min. | 125° C. | 13.2 |
| 3 | 4.3 | 24 hrs. | 60 min. | 90° C. | 11.0 |
| 4 | 4.3 | 24 hrs. | 15 min. | 125° C. | 11.2 |

As can be seen from reference to Table 2, the evaporative drying can occur at a temperature of either approximately 90° or 125° for varying lengths of time without significantly affecting the absorbency of the resultant sodium carboxymethyl starch. It is noted that aging the solution for 24 hours produces a sodium carboxymethyl starch having a lower degree of absorbency. It is hypothesized that this occurs because the acidified solution has time to equilibrate the acid groups uniformly along the polymer chain resulting in more effective crosslinking.

EXAMPLE 5

Thirty-seven and one half grams of ordinary corn starch is slurried in 150 milliliters of water to form a starch solution. To the starch solution is added 12.75 grams of sodium hydroxide which has been dissolved in 75 milliliters of water to form an alkaline starch solution. The alkaline starch solution is stirred for 30 minutes. To the alkaline starch solution is then added 14.63 grams of monochloroacetic acid which has been dissolved in 15 milliliters of water to form a final solution. The final solution is stirred for 6 hours at a temperature of 60° C. The pH is found to level off at approximately 12.23 after approximately 2 hours. The sodium carboxymethyl starch so produced is calculated to have a degree of substitution of approximately 0.67. The final solution is then adjusted to a pH of approximately 5.2 with hydrochloric acid. The sodium carboxymethyl starch is then recovered by evaporative drying in a vacuum oven (90° C., 15 inches of mercury, air bleed) or at 125° C. in a convection oven. The specific time and temperature of the evaporative drying is set forth in Table 3. The sodium carboxymethyl starch thus recovered is subjected to absorbency testing in an aqueous solution containing 1 weight percent sodium chloride according to the process set forth in Example 1. The results in the testing are set forth in Table 3.

TABLE 3

| SAMPLE | pH | DRYING TIME | DRYING TEMPERATURE | ABSORBENCY (g/g) |
|---|---|---|---|---|
| 1 | 5.2 | 2.5 hrs. | 90° C. | 12.7 |
| 2 | 5.2 | 30 min. | 125° C. | 12.5 |

Again, as can be seen from reference to Table 3, so long as the drying occurs within the temperature range described in connection with the instant application the specific temperature employed does not appear to significantly affect the absorbent capacity of the resultant carboxymethyl starch.

EXAMPLE 6

Sodium carboxymethyl starch is prepared according to the process set forth in Example 5 except that 19.1 grams of sodium hydroxide and 21.9 grams of monochloroacetic acid are employed. Additionally, the final solution is maintained at a 55° C. rather than 60° C. The carboxyalkylation appeared to be complete in approximately 2 hours and 45 minutes as evidenced by the fact that the pH leveled off at approximately 12.65. The final solution is calculated to be 17.7% sodium carboxymethyl starch by weight and is calculated to have a degree of substitution of 1.0. The final solution, upon cooling to room temperature was found to have a pH of approximately 13.3. Three samples of the solution are isolated with two of the samples having their pH lowered by addition of hydrogen chloride. The exact pH's employed are set forth in Table 4. The three samples are then dried for 2 or 2½ hours at 90° C. in a vacuum oven (15 inches mercury, air bleed). The sodium carboxymethyl starch thus recovered is subjected to absorbency testing in an aqueous solution containing 1 weight percent sodium chloride according to the procedure set forth in Example 1. The results of this absorbency testing are set forth in Table 4.

TABLE 4

| SAMPLE | pH | DRYING TIME | DRYING TEMPERATURE | ABSORBENCY (g/g) |
|---|---|---|---|---|
| 1 | 13.3 | 2 hrs. | 90° C. | 39.3 |
| 2 | 13.0 | 2.5 hrs. | 90° C. | 15.5 |
| 3 | 11.1 | 2.5 hrs. | 90° C. | 10.5 |

As can been seen from reference to Table 4 the pH of the solution prior to drying can have an affect on the absorbency of the final product.

EXAMPLE 7

A final solution of sodium carboxymethyl starch is prepared in accordance with the procedure of Example 6. Prior to cooling to room temperature or drying, 160 grams of the final solution (17.7% solids) is isolated. To the isolated solution is added 20 grams of ordinary corn starch. The resultant solution is maintained at 70° C. for two hours with stirring. After two hours, the solution is allowed to cool to room temperature and divided into two samples. One of the samples has a pH of about 13 with the other sample being adjusted to a pH of 10.3 with hydrochloric acid. The sodium carboxymethyl starch present in each of the samples is then recovered by drying in a vacuum oven (15 inches of mercury, air bleed) at 90° C. for two hours. The recovered sodium carboxymethyl starch is then subjected to absorbency testing in an aqueous solution containing 1 weight percent sodium chloride as set forth in Example 1. The results of the absorbency testing are set forth in Table 5.

TABLE 5

| SAMPLE | pH | ABSORBENCY (g/g) |
|---|---|---|
| 1 | 13 | 19.6 |
| 2 | 10.3 | 14.0 |

As can be seen with reference to Tables 4 and 5, the addition of a filler of ordinary starch to form a starch grafted cross-linked sodium carboxymethyl starch produces an end product having an absorbency at an equivalent pH and drying conditions which is somewhat better than the ungrafted sodium carboxymethyl starch.

As is apparent from the foregoing specification, the present invention is susceptible of being embodied with various alterations and modifications which may differ particularly from those that have been described in the preceding specification and description. For this reason, it is to be understood that all of the foregoing is intended to be merely illustrative and is not to be construed or interpreted as being restrictive or otherwise limiting of the present invention, accepting as it is set forth and defined in the following claims.

What is claimed is:

1. A method for forming a water-swellable, water-insoluble carboxyalkyl starch having a degree a substitution between about 0.25 and 1.5, said method comprising the steps of:
    (a) forming an aqueous dispersion of starch comprising from about 10 to about 40 weight percent starch based on total weight of the aqueous dispersion;
    (b) adding to said aqueous dispersion an amount of carboxyalkylating reactants under conditions sufficient to form a water-soluble carboxyalkyl starch having an average degree of substitution between about 0.25 and 1.5; and
    (c) recovering the carboxyalkyl starch by evaporative drying at a temperature within the range of from about 50° to about 150° C. whereby the caboxyalkyl starch cross-links.

2. The method according to claim 1 wherein the aqueous dispersion comprises from about 15 to about 30 weight percent starch based on total weight of the aqueous dispersion.

3. The method according to claim 1 wherein the carboxyalkylating reactants comprise an ammonium or alkali metal hydroxide.

4. The method according to claim 3 wherein the alkali metal hydroxide is selected from the group consisting of sodium hydroxide, potassium hydroxide, and lithium hydroxide.

5. The method according to claim 1 wherein the carboxyalkylating reactants comprise a haloalkanoic acid.

6. The method according to claim 5 wherein the haloalkanoic acid is selected from the group consisting of monohaloacetic acid, monohalomaleic acid, monohalomalonic acid and monohalosuccinic acid.

7. The method according to claim 6 wherein the haloalkanoic acid is monochloroacetic acid.

8. The method according to claim 1 wherein the carboxyalkylating reactants comprise an ammonium or alkali metal hydroxide and a haloalkanoic acid.

9. The method according to claim 8 wherein the alkali metal hydroxide is sodium hydroxide and the haloalkanoic acid is monochloroacetic acid.

10. The method according to claim 8 wherein the ammonium or alkali metal hydroxide is added to the aqueous dispersion in an amount of from about 25 to about 300 mole percent based on the total amount of starch present in said aqueous dispersion and the haloalkanoic acid is added to the aqueous dispersion in an amount of from about 25 to about 150 mole percent based on total moles of anhydroglucose repeating units present in the starch present in said aqueous dispersion.

11. The method according to claim 1 wherein the carboxyalkylating reactants are added to the aqueous dispersion which dispersion is then maintained at a temperature within the range of from about 25° to about 100° C. for a period of from about 2 to about 24 hours.

12. The method according to claim 1 wherein the pH of the carboxyalkyl starch containing aqueous solution is adjusted to within the range of from about 13.5 to about 5.

13. The method according to claim 1 wherein the evaporative drying occurs at a temperature within the range of from about 80° to about 125° C.

14. The method according to claim 1 further comprising the step of adding to said aqueous dispersion, after formation of said water-soluble carboxyalkyl starch but before said evaporative drying, an amount of a gelatinized starch.

15. The method according to claim 14 wherein the gelatinized starch is added to said aqueous dispersion in an amount of from about 1 to about 50 weight percent based on total weight of water-soluble carboxyalkyl starch present in said aqueous dispersion.

16. The method according to claim 1 further comprising the steps of adding to said aqueous dispersion, after formation of said water-soluble carboxyalkyl starch but before said evaporative drying, and amount of unmodified starch and subsequently heating said aqueous dispersion to convert said unmodified starch into a gelatinized starch.

17. The method according to claim 16 wherein the unmodified starch is added to said aqueous dispersion in an amount of from about 1 to about 50 weight percent based on total weight of water-soluble carboxyalkyl starch present in said aqueous dispersion.

18. The method according to claim 17 wherein the aqueous dispersion is subsequently heated to from about 70° to about 100° C.

19. A method for forming a water-swellable, water-insoluble carboxyalkyl starch having a degree of substitution between about 0.25 and 1.5, said method comprising the steps of:

(a) forming an aqueous dispersion of starch comprising from about 10 to about 40 weight percent starch based on total weight of the aqueous dispersion;

(b) adding to said aqueous dispersion an alkali metal hydroxide in an amount of from about 25 to about 300 mole percent based on the total amount of starch present in said aqueous dispersion and a chloroalkanoic acid in an amount of from about 25 to about 150 mole percent based on the total number of anhydroglucose repeating units present on the starch present in said aqueous dispersion, under conditions sufficient to form a water-soluble carboxyalkyl starch having an average degree of substitution between about 0.25 and 1.5; and (c) recovering the carboxyalkyl starch by evaporative drying at a temperature within the range of from about 50° to about 150° C. whereby the carboxyalkyl starch cross-links.

20. The method according to claim 19 further comprising the step of adding to said aqueous dispersion, after formation of said water-soluble carboxyalkyl starch and before said evaporative drying, gelatinized starch in an amount of from about 1 to about 50 weight percent based on the total weight of water-soluble carboxyalkyl starch present in said aqueous dispersion.

21. The method according to claim 19 further comprising the steps of adding to said aqueous dispersion, after formation of said water-soluble carboxyalkyl starch and before said evaporative drying, unmodified starch in an amount of from about 1 to about 50 weight percent based on the total weight of water-soluble carboxyalkyl starch present in said aqueous dispersion and subsequently heating said aqueous dispersion to a temperature of from about 70° to about 100° C.

22. A product formed according to the method of claim 1.

23. A product formed according to the method of claim 14.

24. A product formed according to the method of claim 16.

* * * * *